United States Patent
Sood et al.

(10) Patent No.: US 11,007,212 B2
(45) Date of Patent: May 18, 2021

(54) MICROBUBBLE COMPLEXES AND METHODS OF USE

(71) Applicant: General Electric Company, Schenectady, NY (US)

(72) Inventors: Anup Sood, Clifton Park, NY (US); Lisa Anne Lowery, Niskayuna, NY (US); Praveena Mohan, Clifton Park, NY (US); James Edward Rothman, Niskayuna, NY (US); John Donald Burczak, Voorheesville, NY (US); Hae Won Lim, Niskayuna, NY (US)

(73) Assignee: GENERAL ELECTRIC COMPANY, Schenetady, NY (US)

( * ) Notice: Subject to any disclaimer, the term of this patent is extended or adjusted under 35 U.S.C. 154(b) by 109 days.

(21) Appl. No.: 16/016,963

(22) Filed: Jun. 25, 2018

(65) Prior Publication Data

US 2019/0060347 A1    Feb. 28, 2019

Related U.S. Application Data

(60) Division of application No. 15/219,419, filed on Jul. 26, 2016, now Pat. No. 10,004,760, and a
(Continued)

(51) Int. Cl.
*A61K 47/64*   (2017.01)
*A61K 31/713*  (2006.01)
(Continued)

(52) U.S. Cl.
CPC .......... *A61K 31/713* (2013.01); *A61K 9/0019* (2013.01); *A61K 41/0028* (2013.01);
(Continued)

(58) Field of Classification Search
None
See application file for complete search history.

(56) References Cited

U.S. PATENT DOCUMENTS

| 6,245,747 B1 | 6/2001 | Porter et al. |
| 2002/0071843 A1* | 6/2002 | Li .......................... A61P 19/10 424/155.1 |

(Continued)

FOREIGN PATENT DOCUMENTS

| CN | 1234742 A | 11/1999 |
| WO | 9854993 A1 | 12/1998 |

OTHER PUBLICATIONS

Wolfrum et al., "Mevchanisms and Optimization of in vivo Delivery of Lipophilic siRNAs", Nature Biotechnology, vol. 25, No. 10, pp. 1149-1157, Oct. 2007.
(Continued)

*Primary Examiner* — Joel F Brutus
(74) *Attorney, Agent, or Firm* — Jeff B. Vockrodt; Culhane Meadows, PLLC

(57) ABSTRACT

The present invention relates to a microbubble complex comprising a microbubble having an outer shell comprising a mixture of native and denatured albumin encapsulating a perfluorocarbon gas, a therapeutic agent, a bifunctional linker having one end attached to the therapeutic agent and the other attached to a ligand and wherein the ligand is bound to the other shell of the microbubble through hydrophobic interactions. Also included are methods for delivering the aforementioned microbubble complex to a tissue target.

6 Claims, 6 Drawing Sheets

Specification includes a Sequence Listing.

Related U.S. Application Data continuation of application No. 13/528,399, filed on Jun. 20, 2012, now abandoned, and a continuation-in-part of application No. 13/235,890, filed on Sep. 19, 2011, now abandoned.

(51) Int. Cl.

| | | |
|---|---|---|
| *A61K 47/54* | (2017.01) | |
| *A61K 47/69* | (2017.01) | |
| *A61K 41/00* | (2020.01) | |
| *C12N 15/87* | (2006.01) | |
| *C12N 15/11* | (2006.01) | |
| *A61K 9/00* | (2006.01) | |
| *A61K 47/06* | (2006.01) | |
| *A61M 37/00* | (2006.01) | |
| *C12N 15/113* | (2010.01) | |

(52) U.S. Cl.
CPC ............ *A61K 47/06* (2013.01); *A61K 47/554* (2017.08); *A61K 47/64* (2017.08); *A61K 47/643* (2017.08); *A61K 47/6925* (2017.08); *A61M 37/0092* (2013.01); *C12N 15/111* (2013.01); *C12N 15/1136* (2013.01); *C12N 15/87* (2013.01); *A61M 2037/0007* (2013.01); *C12N 2310/14* (2013.01); *C12N 2310/3515* (2013.01); *C12N 2320/32* (2013.01)

(56) References Cited

U.S. PATENT DOCUMENTS

| | | | |
|---|---|---|---|
| 2003/0147812 A1* | 8/2003 | Ueberle | A61B 8/481 424/9.52 |
| 2006/0241071 A1* | 10/2006 | Grinstaff | C07C 219/06 514/44 R |
| 2008/0114287 A1 | 5/2008 | Lai et al. | |
| 2008/0319375 A1 | 12/2008 | Hardy | |
| 2010/0172844 A1 | 7/2010 | Neri et al. | |

OTHER PUBLICATIONS

China Office Action and Search Report corresponding to Chinese Application No. 201710959069.0, dated Jan. 2, 2020.

Sirsi, Shashank, et al., "Microbubble Compositions, Properties and Biomedical Applications", National Institutes of Health, Bubble Sci Eng Technol, Nov. 2009, 28 pages.

* cited by examiner

MICROBUBBLE COMPLEXES AND METHODS OF USE

CROSS-REFERENCE TO RELATED APPLICATIONS

This application is a division of U.S. patent application Ser. No. 15/219,419, filed Jul. 26, 2016, now co-pending, which is a continuation of U.S. patent application Ser. No. 13/528,399, filed Jun. 20, 2012, which is a continuation-in-part of U.S. patent application Ser. No. 13/235,890, filed Sep. 19, 2011, the entire disclosures of which are incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 28, 2012, is named 250944-2.txt and is 833 bytes in size.

BACKGROUND

The invention relates generally to novel binding of therapeutic agents to albumin microbubble pharmaceuticals using an attachment of albumin affinity ligands to the agents. The binding provides a method of microbubble-assisted delivery of therapeutic agents to targeted cells or tissue of interest, either in vitro or in vivo.

Ultrasound-mediated destruction of microbubbles carrying drugs has been found to be useful as a noninvasive drug delivery system. Drugs or other therapeutic agents can be incorporated into the microbubbles in a number of different ways, including binding of the drug to the microbubble shell and attachment of ligands. For example, perfluorocarbon-filled microbubbles are sufficiently stable for circulating in the vasculature as blood pool agents; they act as carriers of these agents until the site of interest is reached. Ultrasound applied over the skin surface can then be used to burst the microbubbles at this site, causing localized release of the drug or therapeutic agents on site specific locations.

More specifically, albumin microbubbles have been used and delivered to a specific organ target by site-directed acoustic ultrasound. Albumin is a major protein in blood, and its natural physiological role is to bind and carry a wide variety of lipophilic/poorly soluble ligands throughout the body. These ligands, which may have an affinity to albumin, include fatty acids and other biosynthetic and catabolic products that are hydrophobic in nature. As such albumin microbubbles have been used to carry a variety of therapeutic agents based on proteins and other biologics including, oligonucleotides (ODN) and polynucleotides such as antisense ODN, with sequences complementary to a specific targeted messenger RNA (mRNA) sequence. These microbubble-nucleic acid complexes may be generated from unmodified ODN that are mixed with albumin or lipid components during microbubble shell formation or alternatively, the complex formation can be performed by mixing preformed microbubbles with an ODN of interest. In both cases, the ODN acts as a mechanistic intervention in the processes of gene translation or an earlier processing event. The advantage of this approach is the potential for gene-specific actions which should be reflected in a relatively low dose and minimal non-targeted side effects.

However, a key barrier to translating the potent biology of ODN into drugs is known to be at the level of drug delivery with efficacy and safety. For example, ODN delivery with chemical formulation, viral vectors, and particle delivery have been hampered with clinical safety related problems before therapeutic efficacy can be attained. Furthermore, the use of albumin microbubbles as a carrier of ODNs such as siRNA is limited due to the limited binding of the ODNs to the albumin microbubble as well as the stability of the albumin-ODN complex. Due to negative shell surface potential of albumin, the negatively charged shorter nucleic acids do not bind very well to the microbubble and gene transfection efficiencies using these complexes are generally suboptimal.

Thus there is a need to improve the binding of the therapeutic agents to the microbubble as well as improving the stability and efficacy of the microbubble complex.

Furthermore there is a need to reduce toxicity in the selective delivery of highly cytotoxic drugs. Non-targeted delivery of these drugs can cause systemic toxicity and has prevented the use of many of these drugs all together or at higher doses required for good efficacy. Attempts to deliver these as pro-drugs in many cases have reduced this problem, however, selective uptake in the targeted tissue is not always easy to achieve as most of the uptake mechanisms in the diseased tissue are also present in the normal tissue. Enhancing the uptake of these drugs in selective tissues by non-natural mechanisms as disclosed herein, therefore can add considerable value.

BRIEF DESCRIPTION

Provided herein are novel compositions and methods for increased binding of therapeutic drugs to microbubbles using the affinity of ligand-therapeutic compositions towards the albumin shell.

Systemic circulation of the microbubbles carrying the therapeutic composition can be easily visualized through ultrasound imaging. Therapeutic agent is released from the microbubbles using a trigger of high energy pulsed ultrasound specific to the site of treatment. The cavitation of microbubbles causes sonoporation of the neighboring cells/tissue.

In one embodiment a microbubble complex is disclosed comprising a microbubble having an outer shell comprising a mixture of native and denatured albumin and a hollow core encapsulating a perfluorocarbon gas, a therapeutic agent selected from the group comprising a small molecule chemotherapeutic agent, a peptide, a carbohydrate, or an oligonucleotide, and a bifunctional linker having one end attached to the therapeutic agent and the other attached to the ligand through reaction of a reactive group on the ligand. The ligand is bound to the outer shell of the microbubble through hydrophobic interactions.

In another embodiment a method is for delivering the aforementioned microbubble complex to a tissue target is disclosed. The method comprising the steps of providing the microbubble complex, administrating the microbubble complex to a subject wherein the subject is the source of the tissue target, and administering ultrasonic energy to the subject, wherein the ultrasound energy is sufficient to cause cavitation of the microbubble complex in the tissue target.

BRIEF DESCRIPTION OF THE FIGURES

These and other features, aspects, and advantages of the present invention will become better understood when the following detailed description is read with reference to the accompanying figures wherein.

DETAILED DESCRIPTION

Figure 1:
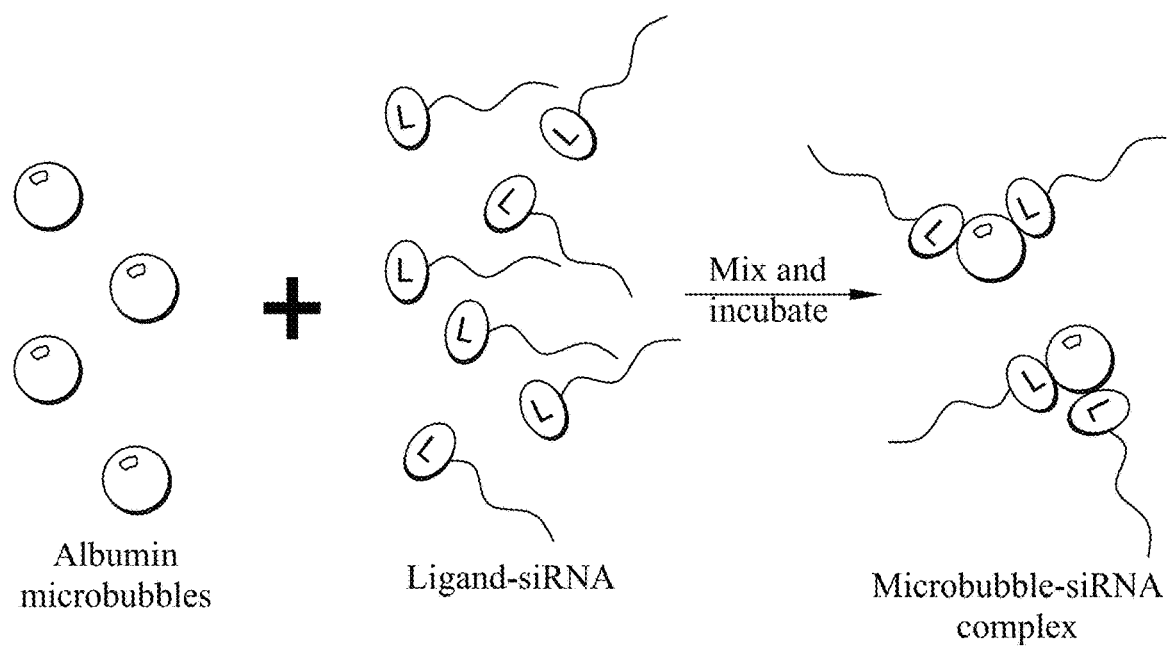
FIG. 1 is a representation of non-covalent binding of siRNA-ligand to albumin microbubbles.

The following detailed description is exemplary and not intended to limit the invention of the application and uses of the invention. Furthermore, there is no intention to be limited by any theory presented in the preceding background of the invention or descriptions of the drawings.

The invention relates generally to microbubble-assisted delivery of a therapeutic agent to cells or tissue of interest, either in vitro or in vivo.

In certain embodiment the therapeutic agent may be comprised of a small molecule chemotherapeutic agent, a peptide, a carbohydrate, or an oligonucleotide, and a bifunctional linker having one end attached to the therapeutic agent and the other attached to the ligand through reaction of a reactive group on the ligand. In certain embodiment the therapeutic agent may be an oligonucleotide (ODN). Oligonucleotides refers to nucleic acid polymers that are formed by bond cleavage of longer nucleic acids or are synthesized using building blocks, protected phosphoramidites of natural or chemically modified nucleosides or, to a lesser extent, of non-nucleosidic compounds. The length of the oligonucleotide may vary from a short nucleic acid polymer of fifty or fewer base pairs to more than 200 base pairs. As used herein, ODN also refers to polynucleotides having more than 200 base pairs. Also included are antisense ODN which refer to single strands of DNA or RNA that are complementary to a chosen sequence. In the case of antisense RNA, antisense RNA prevents protein translation of certain messenger RNA strands by binding to them. Antisense DNA can be used to target a specific, complementary (coding or non-coding) RNA. Also included are small interfering RNA (siRNA), sometimes known as short interfering RNA or silencing RNA, is a class of double-stranded RNA molecules, typically 20-25 nucleotides in length, that play a variety of roles in biology including the RNA interference (RNAi) pathway, where it interferes with the expression of a specific gene, as an antiviral mechanism, or in shaping the chromatin structure of a genome.

In certain embodiments, the therapeutic agent may be a cytotoxin. As used herein cytotoxin refers to a substance that has a toxic effect on cells. For example a cytotoxin may cause undergo necrosis, in which they lose membrane intearity and die as a result of cell lysis. In other examples a cytotoxin may be associated with antibody-dependent cell mediated cytotoxicity wherein a cell is marked by an antibody and acted upon by certain lymphocytes.

Examples of cytotoxic agents are listed in Goodman and Gilman's "The Pharmacological Basis of Therapeutics," Tenth Edition, McGraw-Hill, New York, 2001. These include taxol; nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as alrenocortisteroids (prednisone), progestins (hydroxyprogesterone caproate, medroprogesterone acetate and meaestrol acetate), estrogens (diethylstilbestrol and ethinyl estradiol), antiestrogens (tamoxifen), and androgens (testosterone propionate and fluoxymesterone).

Drugs that interfere with intracellular protein synthesis, protein synthesis inhibitors, can also be coupled to the ligand; such drugs are known to these skilled in the art and include puromycin, cycloheximide, and ribonuclease.

In one embodiment, the protein includes, but is not limited to, enzymes, soluble and serum proteins, proteins expressed on a surface of a cell, non-immunoglobulin proteins, intracellular proteins, and segment of proteins that are or can be made water-soluble, either individually or in combinations thereof as well as any derivatives of the proteins.

In a particular embodiment, the protein includes such as, but not limited to, cysteine proteases, glutathione S transferase, epoxide hydrolase (EH), thiolase, NAD/NADP-dependent oxidoreductase, enoyl coA hydratase, aldehyde dehydrogenase, hydroxypyruvate reductase, tissue transglutaminase (tTG), formiminotransferase cyclodeaminase (FTCD), aminolevulinate-dehydratase (ADD), creatin kinase, carboxylesterase (LCE), monoacylglycerol (MAG) lipase, metalloproteases (MP), phosphotases (protein tyrosine phosphotases, PTP), proteosome, FK506 binding protein (FKBP12), mammalian target of Rapamycin (mTOR; alternatively known as FKBP-rapamycin binding domain (FRB)), serine hydrolase (superfamily), ubiquitin-binding protein, -galactosidase, nucleotide binding enzymes, protein kinases, GTP-binding proteins, cutinase, adenylosuccinate synthase, adenylosuccinate lyase, glutamate dehydrogenase, dihydrofolate reductase, fatty acid synthase, aspartate transcarbamylase, acetylcholinesterase, HMG cholate reductase, and cyclo-oxygenase (COX-1 and COX-2), either individually or in combinations thereof. Also included are any derivatives of any of the proteins.

In another example, the protein is substantially free of a cofactor. "Substantially free of a cofactor" includes proteins that do not require any additional cofactor, chemical, chemical modification, or physical modification to be naturally stable under physiological conditions and room temperature and pressure in solution or as a solid, and can bind its corresponding ligand in vivo.

In one embodiment, an albumin microbubble may be utilized to carry a therapeutic agent in systemic delivery. Tissue targeted ultrasound acoustic energy may then be used to cavitate the albumin microbubble and deliver the therapeutic agent into the intracellular environment. For example the microbubble complex may be administered intravenously or into the peritoneum (intraperitoneally) of a subject whose cells or tissues are to be targeted. Once the microbubble complex is carried through the subject to the targeted cell, the ultrasound acoustic energy is delivered. In certain embodiments, visualization of the targeted cells may occur prior to delivering the ultrasound while in still other embodiments visualization may be performed in real time and the cavitation monitored.

In certain embodiments, the albumin outer shell of the microbubble is comprised of both native and denatured albumin held together by mostly cysteine to cysteine bonds. In certain embodiments, the primary composition of the albumin shell is mostly in the native form wherein the denatured portion allows for increased cysteine bond attachments. In certain embodiments the relative amount of denatured albumin to native albumin ranges from approximately 0.5 to 30 wt %. In other embodiments the relative amount is in the range of approximately 1% to 15 wt %. The mixture of native and denatured albumin provides a balance of shell elasticity needed for cavitation, with increased reactive binding sites on the microbubble surface. The microbubbles are formed by sonication of perfluorocarbon gas in the presence of pre-heated albumin solution. A small part of the albumin molecules rearrange during sonication of pre-heated albumin solution and crosslinking occurs through disulfide linkages between albumin molecules. These albumin molecules are believed to be similar in structure to an F form of albumin which has more hydrophobic residues exposed. This allows increased binding sites for hydrophobic interactions.

In certain embodiments, the microbubble may be filled with an insoluble perfluorocarbon gas, such as but not limited to, perfluoromethane, perfluoroethane, perfluoropropane, perfluorobutane, perfluoropentane, or a combination thereof. In certain embodiments, the microbubbles are about 1 to about 5 microns in diameter, the size being optimized to allow circulation through the blood stream.

In certain embodiments, the therapeutic-microbubble complexes comprise a therapeutic agent modified with a linker having a reactive group capable of binding with a ligand having affinity towards albumin. As such, the therapeutic agent may be coupled to albumin though the ligand.

The linker includes any linking moiety that attaches the ligand to the therapeutic agent through a first moiety. The linker can be as short as one carbon or a long polymeric species such as polyethylene glycol, tetraethylene glycol (TEG), polylysine or other polymeric species normally used in the pharmaceutical industry for modulating pharmacokinetic and biodistribution characteristics of therapeutic agents. Other linkers of varying length include C1-C250 length with one or more heteroatoms selected from O, S, N, P, and optionally substituted with halogen atoms. In a particular embodiment, the linker comprises at least one of an oligomeric or polymeric species made of natural or synthetic monomers, oligomeric or polymeric moiety selected from a pharmacologically acceptable oligomer or polymer composition, an oligo- or poly-amino acid, peptide, saccharide, a nucleotide, and an organic moiety with 1-250 carbon atoms, either individually or in combination thereof. The organic moiety with 1-250 carbon may contain one or more heteroatoms such as O, S, N or P and optionally substituted with halogen atoms at one or more places.

The first moiety may simply be an extension of the linker, formed by the reaction of a reactive species on the linker with a reactive group on the therapeutic agent. Examples of reactive species and the reactive group include, but are not limited to, activated esters (such as N-hydroxysuccinimide ester, pentafluorophenyl ester), a phosphoramidite, an isocyanate, an isothiocyanate, an aldehyde, an acid chloride, a sulfonyl chloride, a maleimide an alkyl halide, an amine, a phosphine, a phosphate, an alcohol or a thiol with the proviso that the reactive species and reactive group are matched to undergo a reaction yielding covalently linked conjugates.

In certain embodiments, the reactive moiety may be a primary amine functionality, and as such, the amine modified therapeutic agent may be conjugated to the affinity ligand through reaction of a carboxyl moiety of the ligand. In certain other embodiments, the reactive moiety may be an alcohol attached to the ligand through a phosphate group.

The affinity ligand includes fatty acids, steroids, small aromatic compounds or a combination thereof. Examples of albumin binding molecules may be found in US patent application publication number 2010/0172844, published Jul. 8, 2010.

For example in certain embodiments the affinity ligand is a fatty acid, including but not limited to myristoyl, lithocolic-oleyl, docosanyl, lauroyl, steoroyl, palmitoyl, oleoyl, or linoleoyl. In other embodiments, the lipophilic molecule is a steroid or modified steroid including, cholesterol, cholic acid, lithocholic acid, or chenodeoxycholic acid. In other embodiment, the high affinity molecule is selected from 4-p-iodophenyl-butyric acid and analogs or derivatives thereof. In still other embodiments, the therapeutic agent comprises siRNA, the linker comprises tetraethylene glycol, and the ligand comprises cholesterol.

In certain embodiments, the therapeutic-albumin complexes may be prepared either by sonicating ligand-modified therapeutic agent with albumin or lipid in the presence of perfluorocarbon or by mixing preformed bubbles with ligand modified therapeutic agents. In certain embodiments, these molecules may be attached to therapeutic agents of interest during therapeutic agent synthesis. For example the phosphoramidites of cholesterol may be used to incorporate cholesterol during DNA or RNA synthesis on a nucleic acid synthesizer, or post synthesis by incorporating a reacting moiety.

In certain embodiments, the therapeutic agent is a modified ODN which may be prepared enzymatically by using modified nucleoside triphosphates; modified either with the ligand itself or with a reactive functionality for post synthesis modification with the ligand. Ligand attachment may be at one or both termini, internal to the nucleic acid sequence or at multiple positions depending upon the ODN use. In certain embodiments, where siRNA is the ODN, attachment may be through the 3' OH position.

In certain embodiments, in addition to the ligand, the therapeutic agent, including where the therapeutic agent is ODN, may be selectively modified to protect from nucleases. In certain embodiments, stabilizing modification may include phosphorothioate modification, or 2'-OMe modification.

In certain embodiments, the microbubble complexes may be incubated with cells or the tissue of interest or injected into the body, preferably intravenously, and then cavitated with ultrasound energy at desired site and at a predetermined time or during live imaging.

In certain embodiments, the microbubble complex may be viewed during systemic travel in the blood circulation under normal ultrasound diagnostic imaging. When the bubble arrives on tissue target, in this case the tumor, a series of pulsed acoustic energy waves are sent to the tumor. This creates inertial cavitation on the microbubble, which collapses the microbubble. Cavitation of the microbubble occurs where the acoustic energy is maximally located. This direction is achieved on the ultrasound probe by parameters related to mechanical index force, optimal ultrasound acoustic distance, and dimensions of the ultrasound acoustic sweep. The force generated can then potentially form micropores within the cellular plasma membrane. Typically the pulsed enemy is administered at a frequency of about 0.5 to about 5 MHz.

These micropores, along with the microjetting force created under inertial cavitation, may facilitate the entrance of ODN into the cellular cytoplasmic environment. For example when the ODN is siRNA, siRNA in the intracellular environment will utilize the host machinery to silence mRNA and later protein synthesis. Similarly, where mRNA message acts as an angiogenesis promoting proteins including vascular endothelial growth factor (VEGF), the reduction of VEGF expression in a tumor may halt or slow tumor growth. After microbubble cavitation the dense gas of the microbubble center is exhaled out of the body and the albumin shell is metabolized and excreted via the liver elimination pathway.

In an exemplary embodiment, a bolus of the microbubble complex may be mixed to an optimal ratio from previous therapeutic investigations. Once the mixture of the complex is established, the bolus drug is injected systemically by venous route.

For example in the use of a siRNA-microbubble bolus, the bolus may be monitored in the first pass blood kinetics. The microbubble resonance and thus enhanced ultrasound contrast may be monitored with an ultrasound probe using low diagnostic levels of acoustic energy. During circulation the bolus arrives on organ target. Cardiovascular tissue perfusion may assist in delivering the bolus into deep microvessels with small lumen diameters. By supplying pulsed acoustic energy, sufficient energy may be provided for the microbubble to undergo inertial cavitation. Once the microbubble cavitation is complete the siRNA contents may be delivered across the plasma membrane and into the diseased cell. While in the cytoplasmic intracellular environment the siRNA can have a therapeutic effect.

During microbubble cavitation siRNA entrance into the cell may occur by various mechanisms. For example the siRNA may enter the cell by a: a microjetting force from the collapsing microbubble which can push siRNA into the cytoplasm. Alternatively the mechanism may include microjetting energy or sonoluminescence energy which creates temporary micropores within the plasma membrane to allow for passive diffusion of the siRNA into the cell, or during microbubble resonance before actual cavitation the microbubble bumping into the plasma membrane may push the siRNA in the cell.

As such, the mechanism of microbubble delivery has potential applications in the treatment of a wide variety of diseases, which can include cancer, inflammatory, infectious, cardiovascular, metabolic, autoimmune, and central nervous system diseases. Many of these diseases cannot currently be effectively treated by virtue of targeting molecular mechanisms not accessible to conventional small molecule drugs and monoclonal antibodies.

Experimental

EXAMPLE 1

FIG. 1 is a representation illustration of binding of siRNA to albumin encapsulated microbubbles to form a microbubble-siRNA complex.

The target siRNA for VEGF silencing (vascular endothelial growth factor) were synthesized by IDTDNA technologies. IDTDNA provided lipid modifications such as cholesteryl TEG on the siRNA (Chol-siRNA) as well as dye conjugation.

```
Sense strand:
                                         (SEQ ID NO: 1)
5'-Cy3/GCAUUUGUUUGUCCAAGAUmUmU/3'-Lipid Antisense strand;
                                         (SEQ ID NO: 2)
5'/mAmArA rUrCrU rUrGrG rArCrA rArArC rArArA
rUrGrC/3'
```

Cyanine dye, Cy3 on the siRNA has an excitation wavelength of 550 nm and a peak emission of 580 nm. The siRNA has been labeled with a cy3 dye for easy visualization of siRNA during binding assays and other characterization techniques. Optison™ (GE Healthcare, Chalfont St. Giles, United Kingdom, 10 mg/ml albumin) was centrifuged; the top layer was discarded and the excess albumin solution in the bottom was used for the binding studies. Lyophilized human serum albumin (HSA) powder (Sigma Aldrich, St. Louis Mo.) was dissolved in 1× phosphate buffered saline (PBS) to make a stock solution of 10 mg/mL. Both Optison and native albumin solution dilutions were prepared with 1× PBS. Denatured HSA solution was prepared by heating native ESA solution to 80° C. for 20 minutes.

Binding Reaction:

The stock solutions of cy3-siRNA and cy3-siRNA-cholesterol, 20 μM were prepared in RNAse free water and stored at −20° C. 4 pmoles of cy3-siRNA and 2 pmoles of cholesterol-siRNA solutions were mixed with varying amounts of Optison solution, native HSA and denatured HSA solution, ranging from 0 to 50 pmoles. The reaction buffer was 1× PBS, pH 7.4. The reaction mixture was incubated under dark at 25° C. for 45 minutes. After incubation, ten μL of siRNA mixtures was mixed with 2 μL of Novex® Hi-Density TBE Sample Buffer (5×) (Invitrogen, Carlsbad, Calif., USA).

Gel Electrophoresis:

All the reactions were loaded onto precast 6% nondenaturing polyacrylamide gels (Invitrogen, Carlsbad, Calif., USA). The gel was run at 100 V for 45 min in 0.5× Novex TBE Running buffer (Invitrogen, Carlsbad, Calif., USA). The gels containing either DNA, protein or both were imaged for cy3 fluorescence using a typhoon scanner (Typhoon™9410, GE Healthcare).

Figure 2:
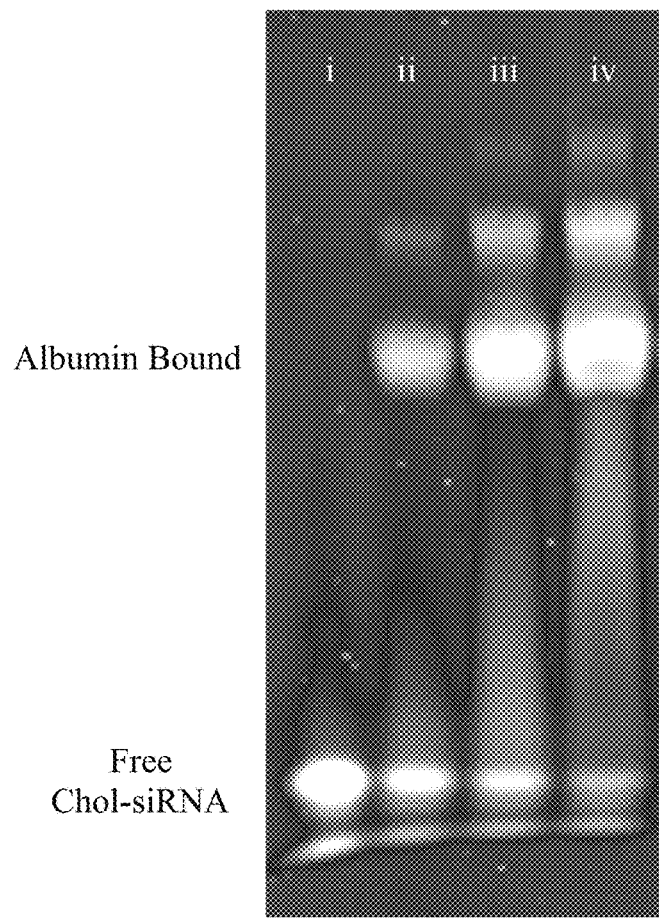
FIG. 2 is representative micrograph of a gel shift assay for a mixture of cholesterol conjugated siRNA (2 pmoles) and varying amounts of Optison (0, 9, 22 and 46 pmoles for i, ii, iii and iv respectively).

Results:

The fluorescence of Cy3 attached to siRNA can be visualized as distinct siRNA bands on the gel. When a mixture of siRNA and albumin solution was run on the gel, the mobility of albumin bound-siRNA is slower than free-siRNA resulting in two bands on the gel. In preliminary trials, sypro ruby stain from EMSA kit (Molecular Probes, Eugene, Oreg., USA) was used to observe the albumin bands in the gel. An example is shown in FIG. 2 which is a gel shift assay for a mixture of cholesterol conjugated siRNA (2 pmoles) and varying amounts of Optison (0, 9, 22 and 46 pmoles for i, ii, iii and iv respectively). Fluorescence imaging of the gel shows distinct bands for siRNA (lower band sections) and albumin (upper band sections).

Cy3-siRNA

Figure 3:
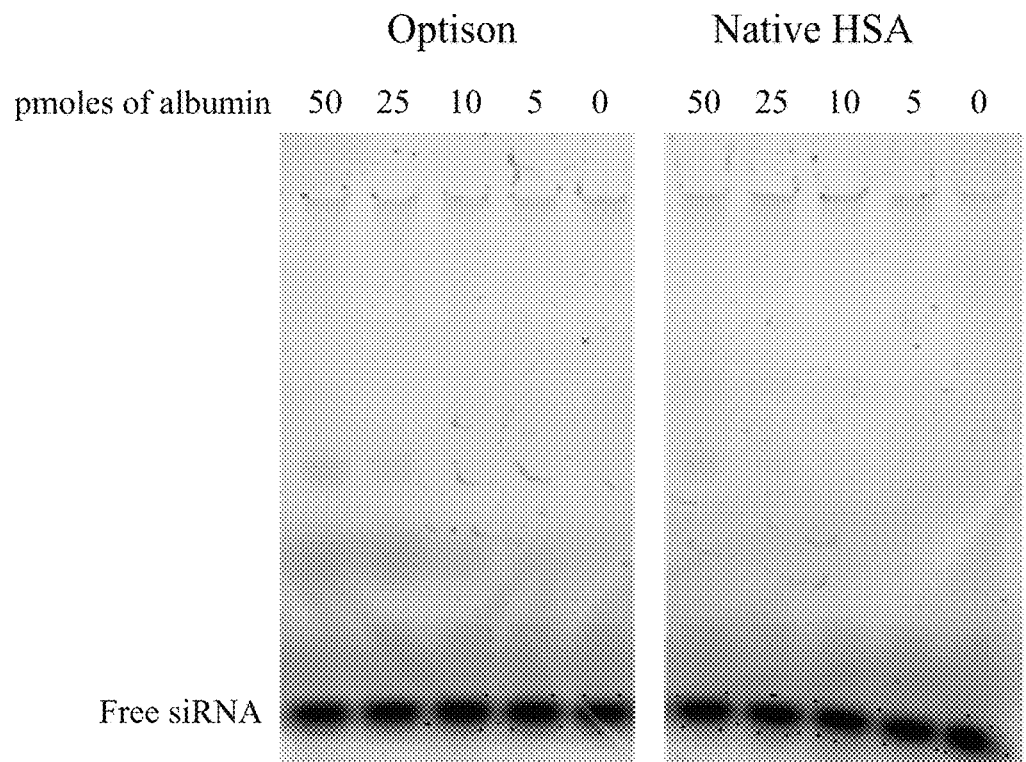
FIG. 3 is a. representative micrograph of a gel shift assay for Cy3-siRNA (4 pmoles) mixed with varying concentrations of either Optison or native HSA which shows no shift in gel assay.

When the mixture of cy3-siRNA and native HSA/Optison was run on the gel, there was no bound-siRNA visualized for increasing concentrations of albumin. There was no significant binding of cy3-siRNA with either native HSA or Optison solution. This is shown in FIG. 3 which is a fluorescence image of a gel for Cy3-siRNA (4 pmoles) mixed with varying concentrations of either Optison or native HSA shows no shift in gel assay. The dark bands on the gel are the cy3-fluorescence on siRNA. There is no significant binding of cy3-siRNA to both Optison and native HSA.

Chol-siRNA

Figure 4:
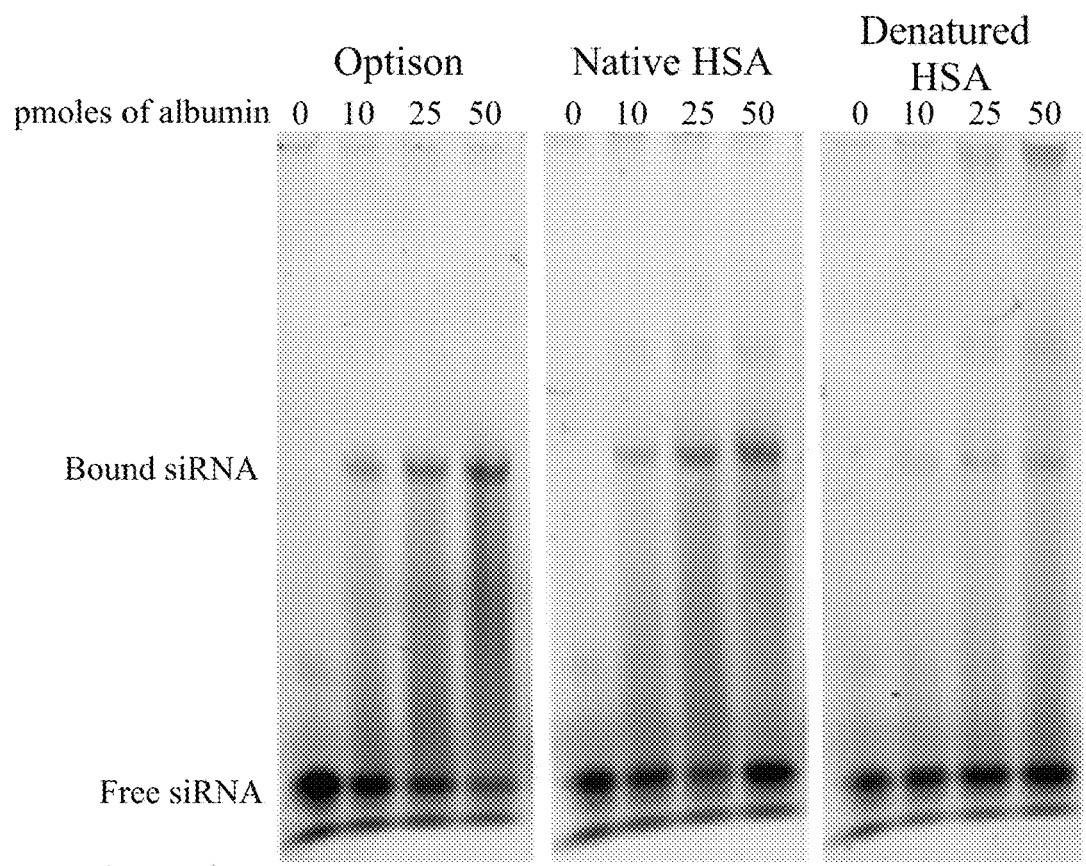
FIG. 4 is a. representative micrograph of a gel assay for Cy3-cholesterol-siRNA (2 pmoles) mixed with varying concentrations of either Optison, native HSA or denatured HSA.

FIG. 4 shows the gel images for binding of chol-siRNA with Optison, native HSA and denatured HSA. Chol bound to both native HSA and Optison solution, while the binding significantly decreased for the same amount of denatured HSA. The fluorescence intensity of siRNA in each lane was estimated manually by drawing a box around the bands. Background, equivalent to the average intensity value of the gel, was subtracted from the intensity value of each siRNA band. Fluorescence intensities of bound siRNA over a wide range of albumin concentrations were calculated. Relative fluorescence, R was calculated as:

$$R = (Fbound - Ffree)/Ffree \quad (1)$$

Figure 5A:
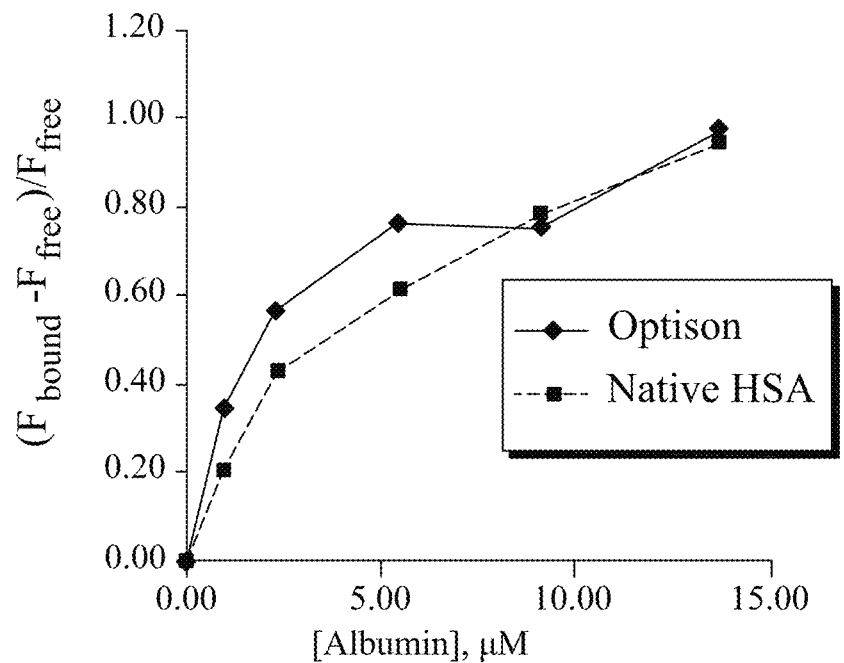
FIGS. 5A and 5B are graphical representations of binding properties of cholesterol-siRNA to Optison and native HSA.
Figure 5B:
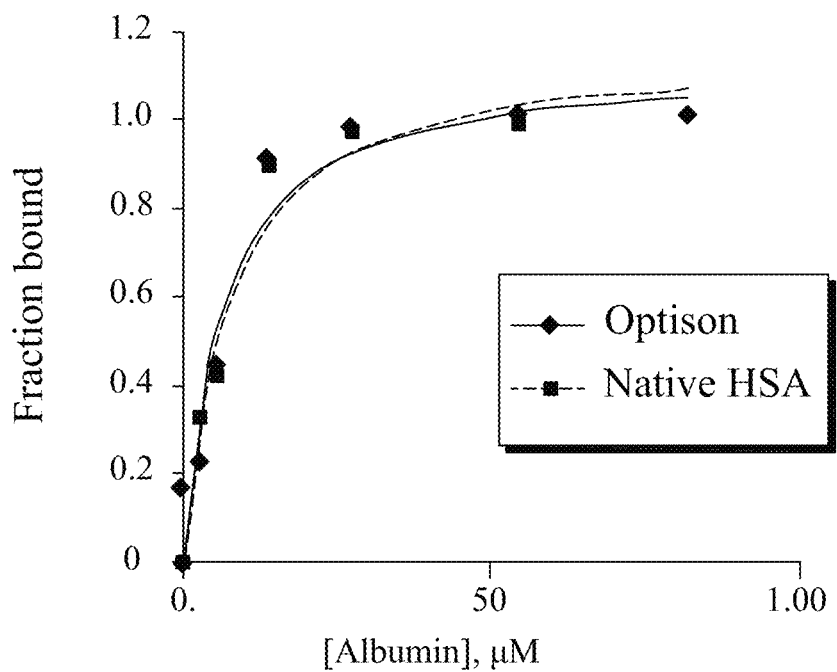

Fbound is fluorescence intensity of bound-siRNA band and Ffree is fluorescence intensity of free-siRNA band. Relative fluorescence was plotted albumin concentration. This is shown in FIGS. 5A and 5B, which are graphical comparisons of binding properties of cholesterol-siRNA to Optison and native HSA as described below.

At low albumin concentration ranging from 0 to 15 μM, linear dependence of bound fluorescence on albumin concentration was visualized. FIG. 5A shows that at this concentration range, the amount of chol-siRNA bound to Optison solution was higher than the binding to native HSA. To estimate binding constants, higher concentration of albumin was used to allow saturation of amount of siRNA bound to albumin. Fraction bound, x is determined as:

$$x = (Fbound - Ffree)/(Fsat - Ffree) \quad (2)$$

Fsat is the fluorescence intensity of maximum bound-siRNA under saturation conditions.

Fraction bound was plotted against increasing albumin concentrations, as shown in FIG. 5B, and the data points were fitted to the following equilibrium equation;

$$x = n*[Albumin]/(kd \pm [Albumin]) \quad (3)$$

kd is the dissociation constant, n is the number of binding sites and [Albumin] is the total albumin concentration for the respective samples. Equation 3 was solved using a non-linear fit to determine kd and n for binding of chol-siRNA to both Optison and native HSA (Table 1). Microsoft Excel's solver tool was utilized for this non-linear fit, and the sum of squared errors (SSE) was found to be 0.07 and 0.06 for Optison and native HSA respectively. The binding constant of chol-siRNA was similar for both Optison and native HSA.

EXAMPLE 2

Delivery of siRNA to Tumor Cells

Cell Culture:

MATBIII rat mammary carcinoma and U-87 human glioblastoma cells were cultured in McCoy's 5A Medium (modified) (1×) (Invitrogen, Carlsbad, Calif., USA) and Eagle's Minimum Essential Medium (EMEM) (ATCC, Manassas, Va.) respectively. Both the media solutions were supplemented with 10% heat deactivated fetal bovine serum (FBS) (Fisher Scientific, Springfield, N.J.) and 1% penicillin-streptomycin (Sigma Aldrich, St Louis, Mo.). The cells were maintained at 37° C. in a humidified atmosphere with 5% CO2.

Sonication of Substrate-Attached Cells:

MATB-III and U-87 cells were grown in 10 mL capacity Opticell units (Nalge Nunc International, Rochester, N.Y.) to 90% confluence. The media in OptiCell was replaced with 10 mL fresh media containing 40 pmoles of either cy3-siRNA or cholesterol-siRNA. The opticell was left in the incubator for 24 hours at 37° C. Separately, the cells were either treated with siRNA solution mixed with Optison microbubbles (300 μL) or a lipid transfection reagent (90 μL) (RNAifect, Qiagen, Valencia, Calif.). For siRNA/Optison mixtures, Vivid i imagers with a cardiac sector probe (3S) was used to rupture the microbubbles and deliver the siRNA drug from microbubbles. The opticell was immobilized in a water bath, and the ultrasound probe was attached to a motion arm that spanned the entire length of the opticell. The tip of the probe was immersed in water, and the distance between the probe and opticell surface was 3 cm that allowed sonication of the entire width of the opticell. The microbubbles in opticell were treated with a mechanical index, MI>1.3 continuous sonication. The probe moved at a speed of 1 m/s over the entire length of the opticell. After sonication, the cells were incubated for 24 hours at 37° C. Similarly, the cells treated with RNAifect were also kept in the incubator for 24 hours. After incubation, the cells were imaged using a fluorescence microscope (Zeiss Axio Imager.Z1, Carl Zeiss). The filter used for cy3 was DsRed/Cy3 (546 ex/620 em). In the region of interest (ROI) in the fluorescent images, cell fluorescence was measured and the mean values of cell fluorescence were calculated. ImageJ was used to process the images and calculate fluorescence intensities.

The data are reported as mean+1.0 standard error (SE) for N=4. The statistical significance of the differences between the groups was evaluated using two-sample t-test and the statistical analyses were carried out using Minitab® 12 (Minitab Inc, State College, Pa. USA).

Figure 6:
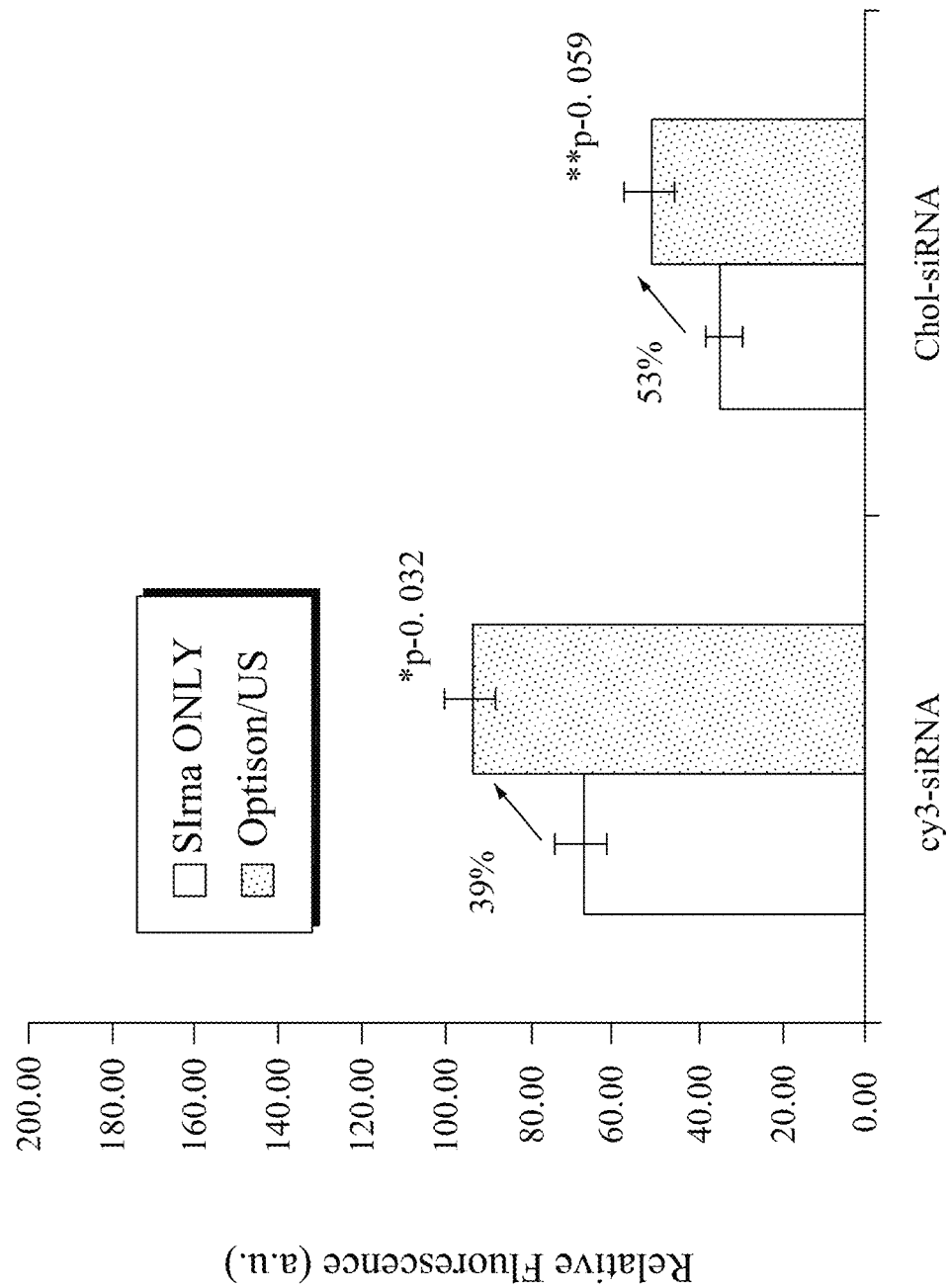
FIG. 6 is a graphical representation of the uptake of siRNA by U-87 tumor cells in opticell is quantified by measuring cell cy3-fluorescence.

Results:

The effect of the delivery system is illustrated in FIG. 6 for U-87 cells incubated with either cy3-siRNA or chol-siRNA. The delivery of siRNA into the tumor cells is represented by average cell cy3-fluorescence. For each group, mean fluorescence values and standard errors are reported in. Cell sonication substantially enhanced cy3-siRNA penetration into the cell. Due to the effects of sonoporation, average cell fluorescence for Optison/ultrasound treated cells was 39% more than untreated cells. For cholesterol-siRNA, there was a 53% increase in average cell fluorescence after treatment with Optison/ultrasound. Significant differences between the groups were evaluated using two sample t-tests (p=0.032 for cy3-siRNA and p=0.059 for cholesterol-siRNA).

Figure 7:
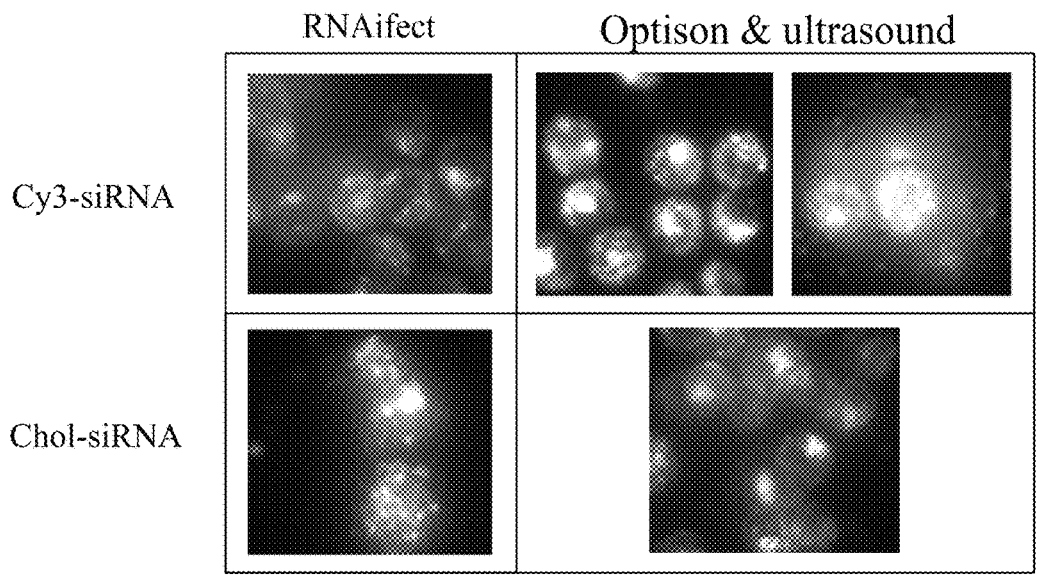
FIG. 7 are micrographs of fluorescence images showing a comparison of siRNA transfection between a lipid transfection reagent (RNAifect) and Optison.
Figure 8:
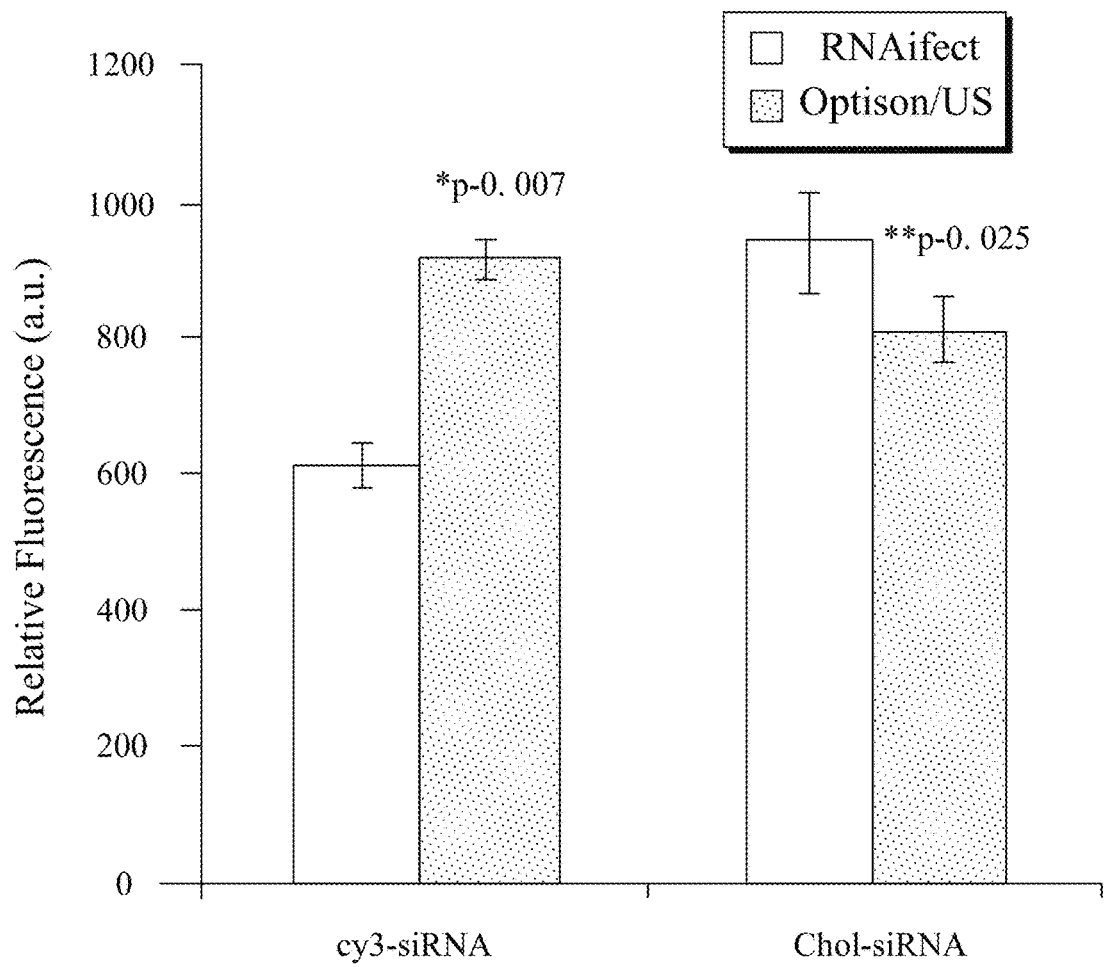
FIG. 8 is a graphical representation of the mean cell fluorescence values and standard error of siRNA transfection between a lipid transfection reagent (RNAifect) and Optison.

Similarly for MATBIII cells, the effect of Optison/ultrasound treatment was compared to a commercially available lipid transfection reagent. The cells were treated with either Cy3-siRNA or chol-siRNA in combination with either RNAifect or Optison/ultrasound delivery agents and the results are shown in FIGS. 7 and 8. FIG. 7 shows representative images of the cells after treatment. FIG. 8 reports the mean cell fluorescence for all groups with standard errors represented as error bars. For cy3-siRNA, the average cell fluorescence was higher for Optison/ultrasound treatment (two sample t-test, p=0.007). This is primarily due to sonoporation of the cells in the presence of microbubbles. There was no significant difference between RNAifect and Optison/ultrasound delivery of chol-siRNA into cells. Although the average cell fluorescence was similar, the lipid transfection reagent was found to be toxic to the tumor cells as evidenced by the irregular shape of the cells in FIG. 7. It should be noted that the same amount of transfection reagent and siRNA was used in both unmodified and cholesterol-siRNA. While the transfection reagent was toxic in both the cases, it was higher for chol-siRNA.

EXAMPLE 3

Preliminary binding studies of therapeutic-fatty acid conjugates to microbubbles were evaluated using fluorescein—fatty acid conjugates.
Conjugation Method;

Fatty acid NHS ester (2 equivalents, 5.37 mg Myristic acid NHS ester or 6.38 mg Stearic acid NHS ester was taken in a 50:50 mixture of DMSO and dichloromethane (100 ul) and mixed with a solution of Fluorescein cadaverine (FL-Cadaverine, 5 mg, 1 equivalent, in 50 ul DMSO). To this diisopropylethyl amine (3.8 equivalents) was added and mixture was vortexed to give a clear solution. Samples were kept in the dark at room temperature. After 4.5 h, reaction was checked by HPLC and was found to be complete. A large shift in retention time was observed for both conjugates (Retention times FL-Cadaverine 4.7 min, FL-Cadaverine stearate 12.1 minute and FL-Cadaverine Myristate 9.9 min, column X-Bridge Shield RP 18, 4.6×50 mm column, particle size 5 um, gradient method 0-100% B in 15 min and 100% B for 5 min, solvent A 0.1M TEAA, pH 7.0 and solvent B 100% acetonitrile, flow rate 1 ml/min) as expected. Crude product was diluted with DMSO to ~2 ml and purified on AKTA purifier using Xterra MS C18, 19×100 mm column and a gradient of 0-100% B in 18.75 column volumes at a flow rate of 10 ml/min. Solvent A and B were as described above for the analytical method. Product was collected in multiple fractions and each fraction was analyzed by analytical HPLC. Only the purest fraction in each case (~90% purity) was used for binding studies (starting material itself was ~86% pure, remaining likely a regioisomer with same spectral properties). This fraction was concentrated to dryness at room temperature. Residue was suspended in water (~2 ml) and extracted with dichloromethane (3×2 ml). Organic extracts were combined, dried over anhydrous sodium sulfate and concentrated to dryness.
Fluorescence Polarization Assay The stock solution of fluorescein-myristate was prepared in 1× PBS. The concentration of fluorescein was kept low for the fluorescence polarization assay, at 126 nM. Varying concentrations of either Optison or HSA solutions, ranging from 0 to 15 µM albumin concentrations, were added to the fluorescein myristate solution. The reaction buffer was 1× PBS, pH 7.4. The reaction mixture was incubated under dark at 25° C. for 15 minutes. After incubation, the changes in raw anisotropy values of fluorescein were measured using a microplate reader (SpectraMax 5, Molecular Devices, Sunnyvale, Calif.).

Figure 9:
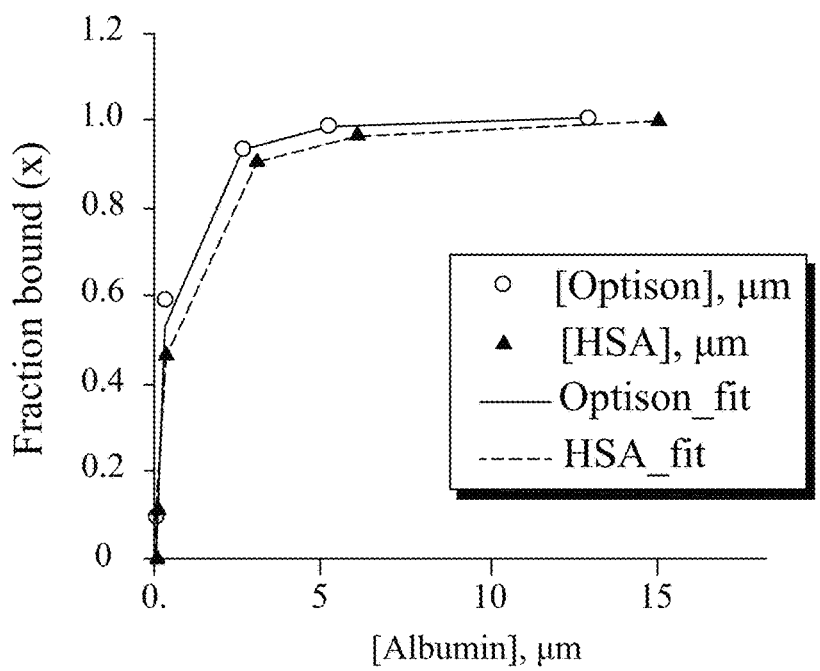
FIG. 9 is a graphical representation of the fraction bound of fluorescein-myristate to Optison and native HSA as calculated from anisotropy values.
Figure 10A:
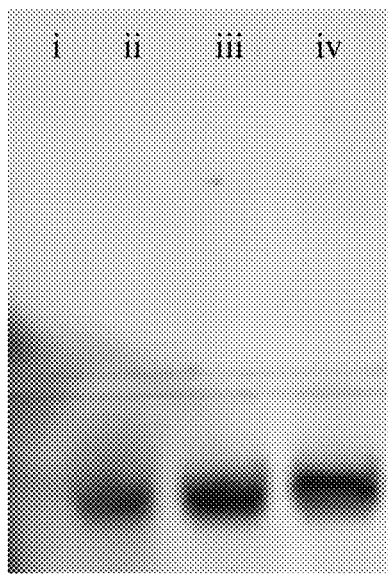
FIGS. 10A and 10B are the fluorescein bound to Optison (0, 8, 40 and 200 pmoles for i, ii, iii and iv respectively) and visualized on the gel as dark bands for fluorescein-myristate (63 pmoles) and fluorescein-stearate (180 pmoles) respectively.
Figure 10B:
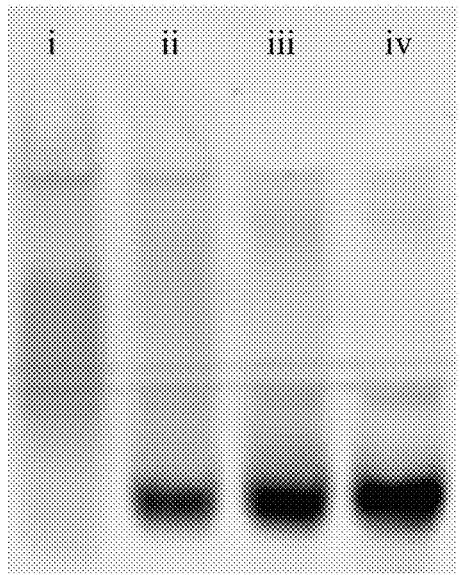

The samples were measured in Corning 96-well plates (black plate with a clear bottom) (Sigma Aldrich, St Louis, Mo.). Fluorescein was excited at 470 nm, and emission was measured at 540 nm. Fraction bound (x) was calculated using the same equation as before (Equation 2), but replacing fluorescence values with anisotropy values. The fraction bound calculated was then plotted against albumin concentration as shown in FIG. 9. The data are reported as mean+1.0 standard error (SE) for N=3. Equation 3 was used to determine kd and n for fluorescein-myristate binding to both Optison and native HSA (Table 2). This is represented also in FIGS. 10A and 10B which show the fluorescein bound to Optison (0, 8, 40 and 200 pmoles for i, ii, iii and iv respectively) is visualized on the gel as dark bands for fluorescein-myristate (FIG. 10A) (63 pmoles) and fluorescein-stearate (FIG. 10B) (180 pmoles).

When the fluorescein without the myristate conjugation was tested for its binding properties to albumin, no significant changes in anisotropy was observed. It is well known that the fatty acids have stronger binding properties than cholesterol, and is also confirmed here with the lower dissociation constants, kd, observed for fluorescein-myristate conjugate (Table 1 and Table 2).

TABLE 1

Number of binding sites and dissociation constants for binding of cholesterol-siRNA to Optison and native HSA

|  | Optison | Native HSA |
|---|---|---|
| Number of binding sites, n | 1.16 | 1.13 |
| Dissociation constant, $k_d$ (µM) | 7.16 | 6.4 |

TABLE 2

Number of binding sites and dissociation constants for binding of fluorescein-myristate to Optison and native HSA

|  | Optison | Native HSA |
|---|---|---|
| Number of binding sites, n | 1.03 | 1.02 |
| Dissociation constant, $k_d$ (µM) | 0.238 | 0.378 |

Therefore, conjugating a fatty acid such as myristate to a therapeutic compound can increase the binding of such therapeutic compounds to the albumin shell microbubbles. The dissociation constant of fluorescein-myristate binding to Optison was lower than that of binding to native HSA. This suggests better hydrophobic binding properties of microbubble shell that has both native and partially denatured albumin.

EXAMPLE 4

Stability of siRNA In Vivo:

The stability of therapeutic compounds such as siRNA is very low once injected into the body. A comparison between subcutaneous and tail-vein injection of a mixture of albumin microbubbles and native siRNA (without conjugates) was studied.

Eleven to fourteen weeks (body weight ~30 g) old nu/nu mice were obtained from Charles River Laboratories (Wilmington, Mass.). Animals were housed in accordance with the Guide for the Care and Use of Laboratory Animals as adopted by the National Institutes of Health. Lewis lung carcinoma cells (LLC) were inoculated subcutaneously to the right flank of anaesthetized mice (3.5×106 cells/100 μl/mouse).

On the fourth day after inoculation, the mice were treated with anti-VEGF siRNA (Sigma Life Sciences, St. Louis, Mo.)—microbubble mixtures, a siRNA dose of 1.0 mg/kg for subcutaneous injections and a dose of 2.0 mg/kg for tail-vein injections. The injection mixture contained 100 μL of microbubble solution and 100 μL of siRNA in RNAse free water. After injection, the tumors were sonicated using Vivid i imagers with a cardiac sector probe (3S). The energies were delivered in a pulsatile form with the peak MI at 1.3. Control group did not receive any treatments.

After 24 hours from the treatment day, the mice were euthanized and the tumors were extracted. The tumors were frozen immediately and stored at −20° C. The tumors were thawed out at room temperature on the day of VEGF measurement. The tumors were then lysed in RIPA buffer (protease inhibitors added) using a lysing matrix tube (Lysing matrix tube A, RP Biomedical). The lysate collected from the samples were then diluted, and measured for total protein using a protein kit (Pierce BCA reagent protein assay kit) and for VEGF using an ELISA kit (Mouse VEGF ELISA kit, RayBiotech, Norcross, Ga.).

The results are reported in Table 3 as mean pg VEGF/mg protein for control and different treatment groups. The subcutaneous injection of 1.0 mg/kg—microbubble mixture resulted in an approximately 39% decrease in VEGF when compared to the control group (two-sample t-test; p=0.0096). While there was only a minor difference between the control group and 2.0 mg/kg tail-vein injection of siRNA-microbubble mixtures, this may be due to lack or less efficient binding of unmodified siRNA to the microbubble.

TABLE 3

The effect of siRNA delivery to tumors; mean pg VEGF/mg total protein.

| Conditions | Mean pg VEGF/mg protein | Std error | 95% Cl | n |
|---|---|---|---|---|
| control | 296.19 | 24.89 | 48.79 | 5 |
| Optison/ siRNA SQ 1 mg/kg | 181.97 | 24.38 | 47.78 | 7 |
| Optison/ siRNA TV 2 mg/kg | 255.1 | 51.06 | 100.07 | 3 |

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method for delivering a microbubble complex to a tissue target comprising the steps of:

providing a microbubble complex, said complex comprising;

a microbubble having an outer shell comprising a mixture of native and denatured albumin and a hollow core encapsulating a perfluorocarbon gas;

a therapeutic agent selected from a small molecule chemotherapeutic agent, peptide, carbohydrate, oligonucleotide, cytotoxin, protein synthesis inhibitor, or combination thereof;

a bifunctional linker having one end attached to the therapeutic agent and the other attached to a ligand through reaction of a reactive group on said ligand; and wherein the ligand is bound to the outer shell of the microbubble through non-covalent, hydrophobic interactions;

administrating the microbubble complex to a subject wherein the subject is the source of the tissue target; and administering ultrasonic energy to the subject, wherein said energy is sufficient to cause cavitation of the microbubble complex in the tissue target.

2. The method of claim 1, wherein the tissue target is in vivo and administrating the microbubble complex comprises intravenous or intraperitoneal injection of the microbubble complex.

3. The method of claim 1, further comprising the step of visualizing the microbubble complex at the tissue target prior to administering the ultrasonic energy for cavitation of the microbubble complex.

4. The method of claim 1, wherein the visualizing and administering the ultrasonic energy are performed in real time.

5. The method of claim 4, wherein the tissue target is in vitro.

6. The method of claim 1, wherein the therapeutic agent comprises siRNA, the linker comprises tetraethylene glycol, and the ligand comprises cholesterol.

\* \* \* \* \*

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gcauuuguuu guccaagauu u                                                 21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaucuugga caaacaaaug c                                                 21
```